(12) United States Patent
Butler

(10) Patent No.: US 8,710,286 B2
(45) Date of Patent: Apr. 29, 2014

(54) OXIDATIVE COUPLING OF HYDROCARBONS AS HEAT SOURCE

(75) Inventor: James R. Butler, League City, TX (US)

(73) Assignee: Fina Technology, Inc., Houston, TX (US)

(*) Notice: Subject to any disclaimer, the term of this patent is extended or adjusted under 35 U.S.C. 154(b) by 889 days.

(21) Appl. No.: 12/416,074

(22) Filed: Mar. 31, 2009

(65) Prior Publication Data

US 2010/0249473 A1    Sep. 30, 2010

(51) Int. Cl.
*C07C 2/78*    (2006.01)

(52) U.S. Cl.
USPC ........... 585/443; 585/304; 585/430; 585/435; 585/440; 585/441

(58) Field of Classification Search
USPC ......... 585/500, 654, 656, 658, 324, 304, 430, 585/435, 440, 441, 443
See application file for complete search history.

(56) References Cited

U.S. PATENT DOCUMENTS

| | | | |
|---|---|---|---|
| 4,950,827 A * | 8/1990 | Erekson et al. | 585/415 |
| 4,950,836 A | 8/1990 | Kimble et al. | |
| 4,982,038 A * | 1/1991 | Kimble et al. | 585/467 |
| 5,012,028 A * | 4/1991 | Gupta et al. | 585/500 |
| 5,025,108 A * | 6/1991 | Cameron et al. | 585/500 |
| 5,118,898 A | 6/1992 | Tyler et al. | |
| 5,254,781 A * | 10/1993 | Calamur et al. | 585/500 |
| 5,750,821 A | 5/1998 | Inomata et al. | |
| 2005/0065392 A1 * | 3/2005 | Peterson et al. | 585/943 |

OTHER PUBLICATIONS

Gradassi et al "Economics of natural gas conversion processes," (1995); Fuel Processing Technology, vol. 42, p. 65-83.

* cited by examiner

*Primary Examiner* — In Suk Bullock
*Assistant Examiner* — Bradley Etherton

(57) ABSTRACT

A process for the coupling of hydrocarbons and utilizing the heat energy produced by the reaction is disclosed. In one embodiment the process can include reacting methane with oxygen to form a product stream containing ethane and further processing the ethane to ethylene in an existing ethylene production facility while using the heat energy produced by the reaction within the facility.

1 Claim, 3 Drawing Sheets

OXIDATIVE COUPLING OF HYDROCARBONS AS HEAT SOURCE

CROSS-REFERENCE TO RELATED APPLICATIONS

Not applicable.

TECHNICAL FIELD

This invention relates generally to processes involving the oxidative coupling of hydrocarbons.

BACKGROUND

Ethylene and ethylene derivatives are widely used in the manufacturing of many of today's plastics. Ethylene is typically obtained by the cracking of hydrocarbons, such as natural gas condensates and petroleum distillates, which include ethane and higher hydrocarbons. Ethylene is then obtained by separation from the cracked product mixture.

Cracking processes are well known in the chemical processing industry. These processes require high temperatures. In the production of ethylene, gaseous, or light liquid hydrocarbons are heated to temperatures ranging from about 750° C. to about 950° C. Typically, in cracking processes to produce ethylene, both ethane and ethylene are produced. The resulting product mixture is usually subjected to elaborate separation steps in order to remove ethylene. This method of producing ethylene is usually very energy intensive.

Multiple separation steps are typically needed in order to recover ethylene from the cracked product stream. These multiple separation steps can be costly in capital expenditures and in energy costs.

Another process that is theoretically possible to produce ethylene is the coupling of methane. Methane is the most abundant component in natural gas and is generally less expensive a feed compared with the typical ethylene cracker feedstock, such as ethane and other higher hydrocarbons. Ethane and ethylene can be produced from methane by the oxidative coupling of methane. In such a process, oxygen and methane are fed into a reactor at elevated temperatures. This process avoids some of the costs associated with cracking processes. However, the reactions involved are highly exothermic and thus such a process is performed under very high temperatures. Such high temperatures can prove difficult in controlling the reaction conditions.

Oxidative coupling also encompasses reactions other than methane coupling, for example, reactions between methane and toluene. These oxidative coupling reactions are also highly exothermic. A need exists to regulate the heat of reaction in order to control the oxidative coupling reaction.

In many processes, including ethylene production processes, steam is utilized to provide necessary heat. Typically steam is produced by combustion of an outside fuel source, such as coal or natural gas, in separate boilers. In certain cracking processes, steam is used to provide the necessary heat for the cracking reaction. Other typical uses for steam include supplying heat to a heat exchanger, supplying heat to a reboiler, and supplying energy to a turbine to drive a compressor. Since typical steam production uses fuel as a heat source, such steam production can be costly, especially when fuel prices are high. A need exists to supply steam in an efficient manner.

In view of the above, it would be desirable to have a process to produce ethylene, which does not rely completely on cracking and expensive separation technologies. It would also be desirable to have an ethylene process that is able to make use of a less expensive feedstock than ethane and heavier hydrocarbons. It would also be desirable to effectively control the exothermic conditions typically associated with methane coupling reactions. In addition, it would be desirable to provide for the generation of steam needed for a process in an efficient manner.

SUMMARY

One embodiment of the present invention is a process that involves reacting oxygen and methane in one or more reactors to form a first product stream comprising ethane and/or ethylene and then further processing at least a portion of the components of the first product stream in at least a portion of an existing ethylene production facility. The first product stream may also contain methane. The process may comprise at least one separation apparatus for at least partial separation of the components from the first product stream. The reactors can include a reaction zone capable of dissipating heat to maintain the reaction zone within a desired temperature range for reacting methane and oxygen to form ethylene and/or ethane.

Methane may be separated from the first product stream creating a second product stream having reduced methane content. The methane may be recycled back to the reactors or may be utilized as heating fuel within the process. At least a portion of the components of the first product stream can be further processed in an ethylene production process. The ethylene production process can include a cracking reactor to form ethylene by subjecting ethane and any other heavier hydrocarbons to cracking conditions.

In another embodiment, the reaction zone capable of dissipating heat is adapted to transfer at least a portion of the heat dissipated to a cracking reactor in the existing ethylene facility. The heat energy recovered can be used to provide steam for use in the existing ethylene facility or to new additions to the facility or for use other than the facility.

Yet another embodiment of the present invention is a process for making ethylene and/or ethane, which includes reacting methane and oxygen in one or more reactors to form a first product stream comprising one or more of ethylene, ethane, and methane; removing at least a portion of any methane from the first product stream to form a second product stream with reduced methane content; separation of at least a portion of the ethane from the first and/or second product stream; and reacting at least a portion of the separated ethane in a cracking reactor to form ethylene. At least a portion of one or more of the separation and cracking processes can be performed utilizing the facilities of an existing ethylene production facility. The one or more reactors may have one or more reaction zones and be capable of dissipating heat to maintain one or more of the reaction zones within desired temperature range (s) to promote the reaction of oxygen and methane to form ethylene and/or ethane. The reaction zone capable of dissipating heat is adapted to transfer at least a portion of the heat dissipated to a cracking reactor in the existing ethylene facility, to new additions to the facility or for other uses.

A further embodiment of the invention is a method for revamping an existing ethylene production facility by adding a process for reacting methane with oxygen to produce a product stream containing ethane and ethylene. The product stream containing ethane and ethylene may then be sent to the existing ethylene product facility for further processing to form additional ethylene. The existing ethylene production facility can include a separation apparatus to remove methane and ethane from the ethylene product stream and a cracking reactor to form ethylene by cracking hydrocarbons. The oxidative coupling reaction can be capable of dissipating heat and at least a portion of the heat dissipated can be recovered and utilized in the existing ethylene production facility, to new additions to the facility or for other uses.

In an embodiment the present invention is a process of an oxidative hydrocarbon coupling reaction that is exothermic and generates heat energy. At least a portion of the heat energy produced by the reaction is recovered and utilized in a facility. The heat energy can generate steam that is utilized in a facility, such as through a distributed steam grid. The steam can be utilized in equipment such as heat exchangers, steam turbines, reboilers, dilution steam and the like. In an embodiment the heat energy produced by the oxidative hydrocarbon coupling reaction is sufficient to supply all the steam needs of a facility.

In alternate embodiments, the reaction can include any oxidative hydrocarbon coupling reaction. In an embodiment, the oxidative coupling reaction includes reactions between methane and toluene. In yet another embodiment, the oxidative coupling reaction includes reactions between isobutylene and methane. In a further embodiment, the oxidative coupling reaction includes reactions between ethylene and methane. In another embodiment, the oxidative coupling reaction includes reactions between methane and t-butyltoluene. In another embodiment, the oxidative coupling reaction includes reactions between methane and trimethylbenzene.

DETAILED DESCRIPTION

Figure 1:
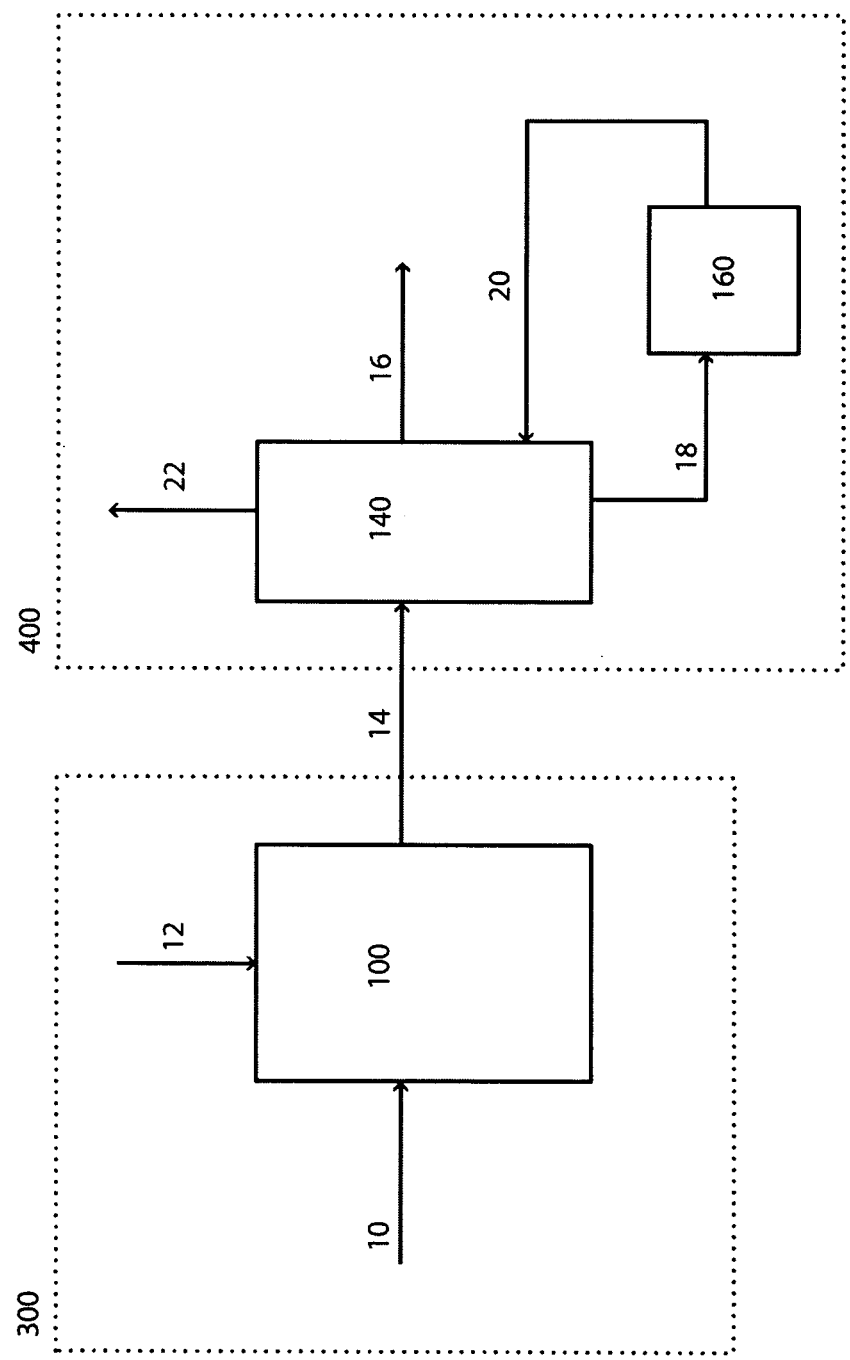
FIG. 1 is a schematic block diagram illustrating a process for making ethylene utilizing methane coupling adapted to an existing ethylene cracking process.

Turning now to the drawings and referring first to FIG. 1, there is illustrated a schematic block diagram of one embodiment of the present invention. A feed stream of methane is supplied via line 10 and input stream of oxygen 12 is supplied to the methane oxidative coupling reaction zone 100. The output from the reaction zone 100 includes a product containing ethane and ethylene, which is supplied via line 14 to a separation zone 140. The separation zone 140 can separate out an ethylene product stream 16 and an ethane stream 18. The ethane stream 18 is sent to a cracking reaction zone 160, where a product stream 20 containing ethylene is obtained from the ethane stream 18. The ethylene stream 20 can be sent to the separation zone 140. Other byproducts can be removed from the separation zone 140 by line 22, this can include methane and other hydrocarbons that can be recycled within the process, used as a fuel gas, flared or otherwise disposed of. Ethylene can be removed from the process from the ethylene product stream 16.

The front end of the process 300 includes the initial oxidative methane coupling reactive zone 100. The input streams to the front end 300 are methane via line 10 and oxygen via line 12. The output stream is the product containing ethylene via line 14 that is sent to the back end of the process 400. The back end 400 includes the separation zone 140 and the cracking zone 160. The front end 300 can be installed to an existing facility. The back end 400 can represent an existing ethylene cracking facility. The product from the front end can be delivered to the existing back end of the facility to complete the process in essentially the same manner as before. The ability to revamp an existing facility and convert from an ethane feedstock to a methane feedstock by the addition of the front end while retaining the existing back end of the facility can have significant economic advantages.

Figure 2:
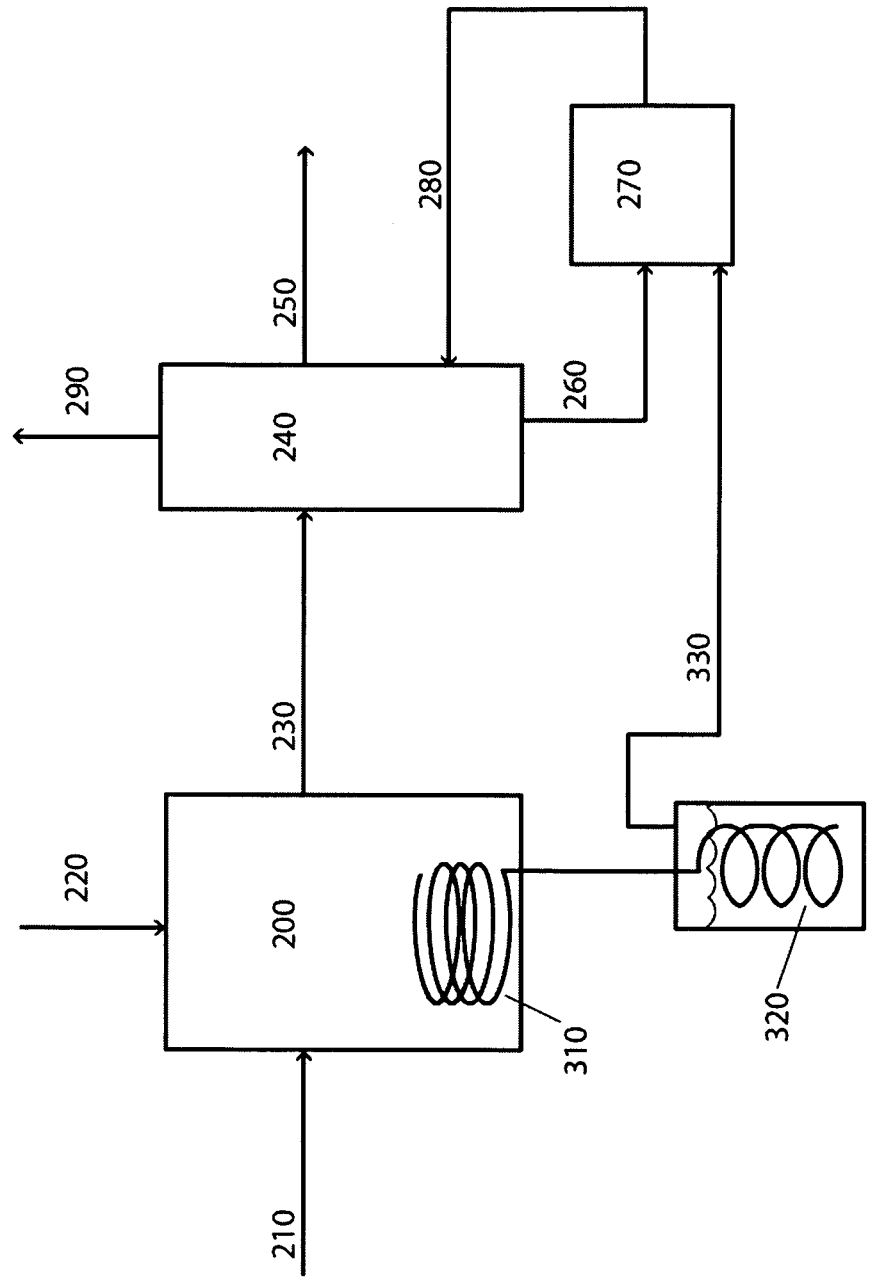
FIG. 2 is a schematic block diagram illustrating a process for making ethylene utilizing methane coupling adapted to an existing ethylene cracking process, where the cracking reactor utilizes heat indirectly from the methane coupling reactor.

Turning now to FIG. 2, there is illustrated a schematic block diagram of an embodiment of the present invention. A feed stream of methane is supplied via line 210 and input stream of oxygen 220 is supplied to the methane oxidative coupling reaction zone 200. The output from the reaction zone 200 includes a product containing ethane and ethylene, which is supplied via line 230 to a separation zone 240. The separation zone 240 can separate out an ethylene product stream 250 and an ethane stream 260. The ethane stream 260 is sent to a cracking reaction zone 270, where a product containing ethylene 280 is obtained from the ethane stream 260. The ethylene stream 280 can be sent to the separation zone 240. Other byproducts can be removed from the separation zone 240 by line 290, this can include methane and other hydrocarbons that can be recycled within the process, used as a fuel gas, flared or otherwise disposed of. Ethylene can be removed from the process from the ethylene product stream 250. A heating coil apparatus 310 is adapted to the reaction zone 200 to withdraw at least a portion of the heat generated by the methane coupling reaction in the reaction zone 200. The heating coil 310 can be used to indirectly generate steam 330 to provide heat for the cracking zone 270. The heating coil 310 transfers heat to a boiler 320, which produces steam 330, which is in turn sent to the cracking zone 270. This heat recovery allows for greater control of the highly exothermic methane coupling reaction, while at the same time reducing energy costs by providing heat for the cracking reaction zone.

Figure 3:
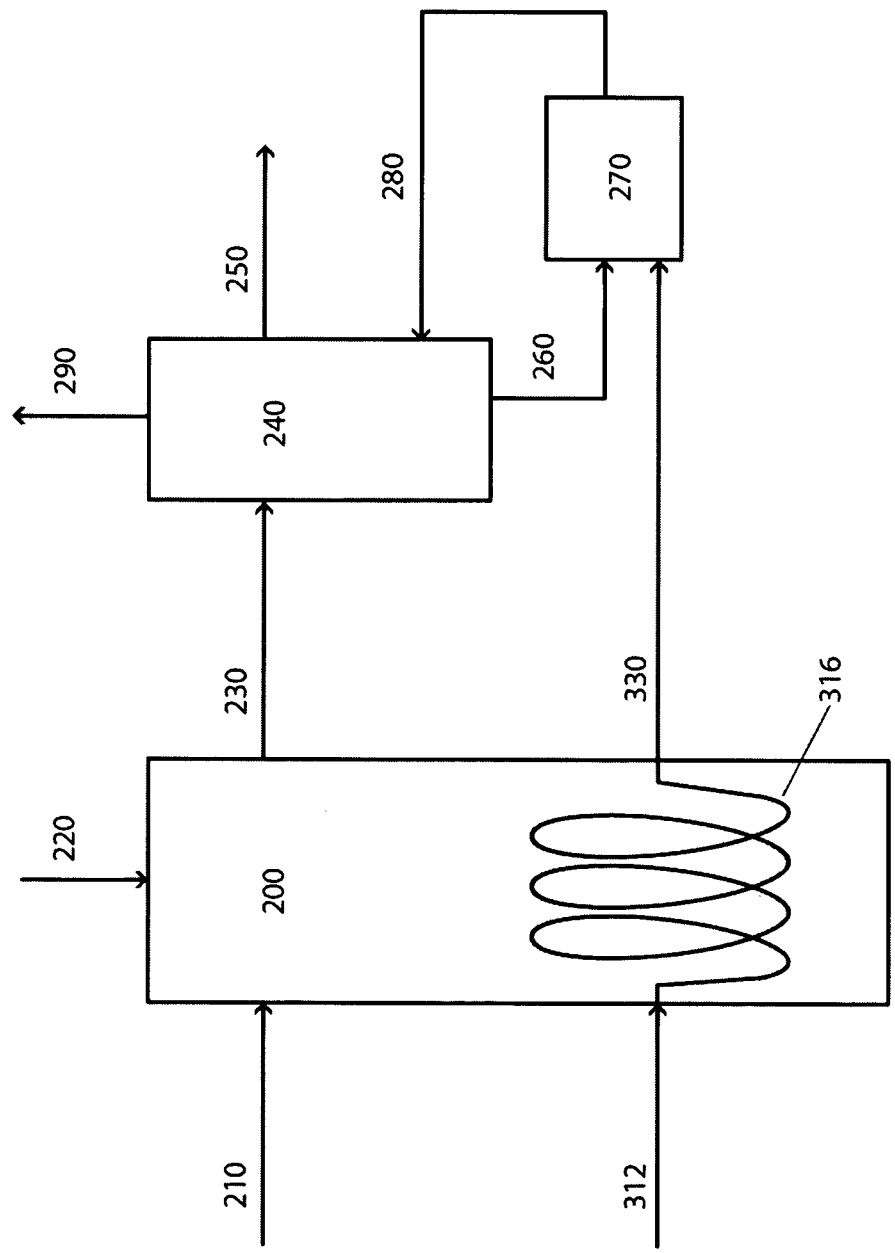
FIG. 3 is a schematic block diagram illustrating a process for making ethylene utilizing methane coupling adapted to an existing ethylene cracking process, where the cracking reactor utilizes heat directly from the methane coupling reactor.

Turning now to FIG. 3, there is illustrated a schematic block diagram of another embodiment of the present invention. A feed stream of methane is supplied via line 210 and input stream of oxygen 220 is supplied to the methane oxidative coupling reaction zone 200. The output from the reaction zone 200 includes a product containing ethane and ethylene, which is supplied via line 230 to a separation zone 240. The separation zone 240 can separate out an ethylene product stream 250 and an ethane stream 260. The ethane stream 260 is sent to a cracking reaction zone 270, where a product containing ethylene 280 is obtained from the ethane stream 260. The ethylene stream 280 can be sent to the separation zone 240. Other byproducts can be removed from the separation zone 240 by line 290, this can include methane and other hydrocarbons that can be recycled within the process, used as a fuel gas, flared or otherwise disposed of. Ethylene can be removed from the process from the ethylene product stream 250. A heating coil apparatus 316 is adapted to the reaction zone 200 to withdraw at least a portion of the heat generated by the methane coupling reaction in the reaction zone 200. The heating coil 316 can be used to directly generate steam 330 to provide heat for zone 270, turbine drivers for the compressors and/or pumps, steam for the reboilers and heat exchangers, or other uses within the process. In an embodiment, zone 270 represents a cracking zone. In another embodiment, zone 270 includes at least one piece of equipment that utilizes steam such as a turbine to drive at least one compressor and/or pump, or at least one reboiler and/or heat exchanger. The heating coil 316 produces steam 330 from a water supply stream 312. This heat recovery allows for greater control of the highly exothermic methane coupling reaction, while at the same time reducing energy costs by providing steam normally produced by separate boilers.

The methane coupling reaction zone of the present invention can include one or more single or multi-stage reactors. Optionally the reactors can be combinations of one or more single or multi-stage reactors in either series or parallel arrangements. Cooling of the reactants and/or products can be provided within the reactors or optionally between the reactors in series. In one embodiment the reactive zone (100, 200) can have a plurality of series-connected reactors. Additionally and in the alternative the reactive zones can be arranged in a parallel manner. There can also be embodiments having multiple series connected reactors that are arranged in a parallel manner. The reactive zone (100, 200) can be operated at temperature and pressure conditions to enable the methane coupling reaction to for ethylene, and at a feed rate to enhance the formation of ethylene. The methane coupling reactor can be operated in the vapor phase. In one embodiment, the methane coupling reaction zone is operated in the vapor phase within a pressure range of atmospheric to 500 psig. Another embodiment can be operated in the vapor phase within a pressure range of atmospheric to 500 psig. Another embodiment can be operated in the vapor phase within a pressure range of atmospheric to 300 psig. Another embodiment can be operated in the vapor phase within a pressure range of atmospheric to 150 psig.

In an embodiment of the invention oxygen is added to the reaction zone (100, 200) in amounts that can facilitate the conversion of methane to ethylene and/or ethane. The oxygen content can range from 1% to 75% by volume relative to the methane content. In another embodiment, the desirable oxygen content can range from 2% to 50% by volume relative to the methane content. In yet another embodiment, the desirable oxygen content can range from 5% to 25% by volume relative to the methane content. In an embodiment of the invention, the reactor of the present invention can include multiple reactors and oxygen can be added to the plurality of series-connected reactors in a manner to enhance ethylene and/or ethane production while retarding the production of undesirable products. Oxygen can be added incrementally to each of the plurality of series-connected reactors as needed to enhance ethylene and/or ethane production, to limit the exotherm from each of the reactors, to maintain oxygen content within a certain range throughout the plurality of reactors or to customize the oxygen content throughout the plurality of reactors. In one embodiment, there is the ability to have an increased or reduced oxygen content as the reaction progresses and the ethylene and/or ethane fraction increases while the methane fraction decreases. There can be multiple series-connected reactors that are arranged in a parallel manner, which can increase overall production capacity and provide for auxiliary reactors to facilitate maintenance and/or regeneration activities.

In the methane coupling reaction zone the oxygen reacts with at least a portion of the methane resulting in an exothermic reaction. The heat generated by the exothermic reaction can be dissipated in many ways, such as for example utilizing an external cooling jacket, internal cooling coils, heat exchange, or by using a reactor such as a Lurgi molten salt type reactor. The heat removed can be controlled in such a manner as to maintain the reaction within a desired temperature range to facilitate the conversion of methane to ethylene and/or ethane. In an embodiment, the desirable temperature range is from 550° C. to 1000° C. In another embodiment, the desirable temperature range is from 600° C. to 800° C.

In another embodiment, the first reaction zone can include any oxidative coupling reaction of hydrocarbons. In another embodiment, the oxidative coupling reaction includes reactions between methane and toluene. In this embodiment, oxygen along with methane and toluene are supplied to the oxidative reaction zone.

In yet another embodiment, the oxidative coupling reaction includes reactions between isobutylene and methane. In this embodiment, oxygen along with methane and isobutylene are supplied to the oxidative reaction zone.

In a further embodiment, the oxidative coupling reaction includes reactions between ethylene and methane. In this embodiment, oxygen along with methane and ethylene are supplied to the oxidative reaction zone.

In yet another embodiment, the oxidative coupling reaction includes reactions between t-butyltoluene and methane. In this embodiment, oxygen along with methane and t-butyltoluene are supplied to the oxidative reaction zone and can produce a product that includes t-butylstyrene.

In another embodiment, the oxidative coupling reaction includes reactions between trimethylbenzene and methane. In this embodiment, oxygen along with methane and trimethylbenzene are supplied to the oxidative reaction zone and can produce a product that includes dimethylstyrene.

At least a portion of the heat generated by the exothermic reaction can be recovered to be utilized within the process. In an embodiment, the heat generated by the exothermic reaction can be utilized in any part of a facility. In a more specific embodiment, at least a portion of the heat generated by the exothermic coupling reaction is removed and recovered to utilized in a following cracking reactor. In another embodiment, the temperature of the coupling reaction can be controlled by adjusting the amount of heat removed from the coupling reaction. In an embodiment the heat energy produced by the oxidative hydrocarbon coupling reaction is sufficient to supply all the steam needs of a facility.

In an embodiment, the recovered heat is supplied to a steam boiler where steam is generated for a steam cracker. In another embodiment, the steam is heated directly in the oxidative reaction zone. The heat generated by the exothermic reaction can be dissipated in many ways, such as for example utilizing an external cooling jacket, internal cooling coils, or direct or indirect heat exchange. The dissipated heat is transferred to a steam boiler, where steam is produced and recovered. The recovered steam is then utilized in the cracking zone.

In an embodiment, the steam generated by the oxidative reaction zone is sent to a steam grid within a facility. The steam grid can be used to supply the generated steam to heat reboilers, supply heat exchangers, to power turbines that drive compressors, and any other useful application in a facility.

In one embodiment the reactive zone (100, 200) of the present invention can comprise one or more single or multi-stage catalyst beds containing catalyst(s). The catalyst that can be used in the reactive zone (100, 200) can include any catalyst that is capable of coupling methane to make ethylene and/or ethane and are not limited to any particular type. In one non-limiting example the catalyst can contain one or more metal oxides. In one non-limiting example the catalyst can contain a metal oxide that is supported on an appropriate substrate. The catalysts may contain different combinations of alkali, alkaline earth, rare earth, and/or transition metal oxides.

As used herein, "between" is defined to mean that the components are arranged in series process flow rather than parallel process flow and that the component referred to is situated after the process flow through one of the reference items and before the process flow through the other reference item. As such, the components do not have to be aligned in a particular physical location with respect to each other.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

As used herein, "parallel" or "parallel arrangement" is defined to mean that the components are not arranged in series and that each component separately processes a portion of the stream. As such, the components do not have to be aligned in a true physical parallel manner with respect to each other.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

The invention claimed is:

1. A process comprising:
an oxidative coupling reaction of hydrocarbons, wherein the oxidative coupling reaction includes the reaction of methane and toluene, isobutylene, t-butyltoluene, or trimethylbenzene;
wherein the oxidative coupling reaction is exothermic and generates heat energy;
wherein at least a portion of the heat energy produced by the oxidative coupling reaction is recovered as steam which is then utilized in an ethylene production facility;
wherein the steam produced by the oxidative coupling reaction is sufficient to supply enough energy to supply all of the steam needs for the ethylene production facility.

* * * * *